(12) United States Patent
Okazoe et al.

(10) Patent No.: US 7,034,179 B2
(45) Date of Patent: Apr. 25, 2006

(54) METHOD FOR PRODUCING A FLUORINATED ESTER COMPOUND

(75) Inventors: Takashi Okazoe, Yokohama (JP); Kunio Watanabe, Yokohama (JP); Shin Tatematsu, Yokohama (JP); Koichi Yanase, Chiba (JP); Yasuhiro Suzuki, Chiba (JP); Daisuke Shirakawa, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 10/397,521

(22) Filed: Mar. 27, 2003

(65) Prior Publication Data

US 2003/0216595 A1    Nov. 20, 2003

Related U.S. Application Data

(63) Continuation of application No. PCT/JP01/08433, filed on Sep. 27, 2001.

(30) Foreign Application Priority Data

Sep. 27, 2000   (JP)   ............................. 2000-295141

(51) Int. Cl.
    *C07C 69/63*   (2006.01)
(52) U.S. Cl. ...................... 560/227; 560/229; 560/219; 560/226
(58) Field of Classification Search ................ 560/226, 560/227, 30, 47, 62, 65, 83, 167, 184, 219
    See application file for complete search history.

(56) References Cited

U.S. PATENT DOCUMENTS

| | | | |
|---|---|---|---|
| 3,900,372 A * | 8/1975 | Childs et al. ................ 205/430 |
| 5,093,432 A | 3/1992 | Bierschenk et al. | |
| 5,322,903 A | 6/1994 | Bierschenk et al. | |
| 5,466,877 A | 11/1995 | Moore | |
| 6,093,860 A | 7/2000 | Watanabe et al. | |
| 6,255,536 B1 | 7/2001 | Worm et al. | |
| 6,586,626 B1 * | 7/2003 | Okazoe et al. ............... 562/863 |
| 2003/0216595 A1 | 11/2003 | Okazoe et al. | |

FOREIGN PATENT DOCUMENTS

| | | |
|---|---|---|
| EP | 0 062 430 | 10/1982 |
| EP | 0 150 618 | 8/1985 |
| JP | 52-010221 | 1/1977 |
| JP | 2-311438 | 12/1990 |
| JP | 2001-139509 | 5/2001 |
| WO | WO 95/25082 | 9/1995 |
| WO | WO 00/56694 | 9/2000 |
| WO | WO 02/10107 | 2/2002 |
| WO | WO 02/18314 | 3/2002 |
| WO | WO 02/44138 | 6/2002 |
| WO | WO 02/055471 | 7/2002 |

OTHER PUBLICATIONS

U.S. Appl. No. 10/397,521, filed Mar. 27, 2003, Okazoe et al.
U.S. Appl. No. 10/727,610, filed Dec. 5, 2003, Okazoe et al.
U.S. Appl. No. 10/833,048, filed Apr. 28, 2004, Okazoe et al.
U.S. Appl. No. 10/915,423, filed Aug. 11, 2004, Okazoe et al.

* cited by examiner

*Primary Examiner*—Johann Richter
*Assistant Examiner*—Karl Puttlitz
(74) *Attorney, Agent, or Firm*—Oblon, Spivak, McClelland, Maier & Neustadt, P.C.

(57) ABSTRACT

The present invention provides a method for producing industrially useful fluorine-containing compounds such as a fluorinated ester compound and an acid fluoride compound.

Namely, the present invention resides in a method for producing a fluorinated ester compound, which comprises fluorinating an ester compound which is an ester of a compound having hydroxyl group(s) with a compound having acyl fluoride group(s) and which has a structure which can be fluorinated, in a liquid phase to produce a fluorinated ester compound, wherein the fluorination is carried out in the form of a liquid mixture of the ester compound and the compound having acyl fluoride group(s).

12 Claims, No Drawings

METHOD FOR PRODUCING A FLUORINATED ESTER COMPOUND

TECHNICAL FIELD

The present invention relates to a method for producing industrially useful fluorine-containing compounds such as a fluorinated ester compound and an acid fluoride compound.

BACKGROUND ART

A fluorinated ester compound having all of C—H portions in a hydrocarbon compound fluorinated to C—F is useful as e.g. a precursor of a fluororesin material. As a method of fluorinating a hydrocarbon compound containing C—H, a method of using cobalt trifluoride, a method of direct fluorination by using fluorine ($F_2$) and a method of carrying out a fluorination reaction by electrolysis of hydrogen fluoride in an electrolyzer (hereinafter referred to as ECF method), have been known.

In a case of carrying out a fluorination reaction by using fluorine in a liquid phase, in an ordinary case, a solvent which does not react with fluorine but dissolves fluorine (such as a solvent consisting of a perfluoro compound) is used as a reaction solvent to form the liquid phase. As a reaction solvent employed in a conventional method, a chlorofluorohydrocarbon such as $CCl_2FCClF_2$ (hereinafter referred to as R-113) or a fluorine type solvent such as a perfluorohydrocarbon or chloroperfluoropolyether (JP-A-4-500520) may be mentioned. Among these solvents, a chlorofluorohydrocarbon has a high ozone depletion potential and thus its production is limited, and it will be no longer available in future. Further, the hydrocarbon compound used as a substrate in the fluorination reaction in many cases has a low solubility in a solvent, whereby the fluorination reaction is carried out at an extremely low concentration, thus leading to a problem of poor production efficiency or a problem such that the reaction is carried out in a suspension system which is disadvantageous to the reaction.

DISCLOSURE OF THE INVENTION

The present inventors have found that in a case of producing a perfluoroester capable of being converted to e.g. a raw material monomer of a fluororesin, such as perfluoro (alkyl vinyl ether), by means of a fluorination reaction in a liquid phase, the reaction process will be very efficiently carried out without any inconvenience such as a decrease in the yield of the fluorination reaction, when an ester compound and an acyl fluoride corresponding to the structure of the ester compound are used. Particularly, they have found that when a partially fluorinated ester having a specific structure is employed as a substrate of the fluorination reaction, the solubility of the substrate in the liquid phase tends to increase, the volume efficiency tends to be high, and the reaction operation tends to be easy, and when a fluorination reaction is carried out in the form of a liquid mixture with a perfluoroacyl fluoride corresponding to the structure of the partially fluorinated ester, a more efficient reaction process can be carried out. Namely, the present invention provides the following production methods.

1. A method for producing a fluorinated ester compound, which comprises fluorinating an ester compound which is an ester of a compound having hydroxyl group(s) with a compound having acyl fluoride group(s) and which has a structure which can be fluorinated, in a liquid phase to produce a fluorinated ester compound, wherein the fluorination is carried out in the form of a liquid mixture of the ester compound and the compound having acyl fluoride group(s).
2. The above method, wherein the ester compound is a compound which is produced by esterification of the compound having hydroxyl group(s) and the compound having acyl fluoride group(s).
3. The above method, wherein the liquid mixture of the ester compound and the compound having acyl fluoride group(s) is obtained by esterification by using the compound having acyl fluoride group(s), wherein the amount of the compound having acyl fluoride group(s) is larger than the stoichiometric amount which is required to esterify all hydroxyl groups in the compound having hydroxyl group(s), and the amount is such an extent that the unreacted compound having acyl fluoride group(s) remains in the reaction product.
4. The above method, wherein the ester compound is the following compound (3), the compound having acyl fluoride group(s) is the following compound (2), and the fluorinated ester compound is the following compound (4):

$$FCOR^{BF} \quad (2)$$

$$R^A CHR^1 OCOR^{BF} \quad (3)$$

$$R^{AF} CFR^{1F} OCOR^{BF} \quad (4)$$

wherein each of $R^A$ and $R^{AF}$ which may be the same or different, is a monovalent organic group, and when $R^A$ and $R^{AF}$ are different from each other, $R^{AF}$ is a monovalent organic group obtained by fluorination of $R^A$. $R^{BF}$ is a perfluoro monovalent saturated organic group. $R^1$ is a hydrogen atom or a monovalent organic group. $R^{1F}$ is a fluorine atom when $R^1$ is a hydrogen atom, when $R^1$ is a monovalent organic group, each of $R^1$ and $R^{1F}$ which may be the same or different, is a monovalent organic group, and when $R^1$ and $R^{1F}$ are different from each other, $R^{1F}$ is a monovalent organic group obtained by fluorination of $R^1$.

5. The above method, wherein the liquid mixture of the compound (3) and the compound (2) is a reaction product obtained by reacting the following compound (1) with the compound (2) in an excess amount to the compound (1):

$$R^A CHR^1 OH \quad (1)$$

wherein $R^A$ and $R^1$ are as defined above.

6. A method for producing the following compound (5) and/or the following compound (2), which comprises a dissociation reaction of the ester bond in the compound (4) obtained by the above method:

$$R^{AF} COR^{1F} \quad (5)$$

$$R^{BF} COF \quad (2)$$

wherein $R^{AF}$ and $R^{1F}$ are as defined above.

7. The above method, wherein the dissociation reaction of the ester bond of the compound (4) is carried out in the form of a liquid mixture of the compound (2) and the compound (4) obtained by a fluorination reaction of the liquid mixture of the compound (3) and the compound (2).
8. The above method, wherein the dissociation reaction of the ester bond is carried out without adding a solvent other than the compound (2) to the liquid mixture of the compound (4) and the compound (2).
9. The above method, wherein a part or whole of the compound (2) obtained by the above method, or when $R^{1F}$ is a fluorine atom, a part or whole of the compound (5) and/or the compound (2), is used as the compound (2) to be reacted with the compound (1).

10. The above method, wherein $R^{AF}$ and $R^{BF}$ are groups having the same structure.

11. The above method, wherein the fluorination in a liquid phase is carried out by reaction with fluorine in a liquid phase.

12. The above method, wherein the fluorination in a liquid phase is carried out in the absence of a solvent other than the compound (2).

BEST MODE FOR CARRYING OUT THE INVENTION

In the present specification, an organic group is a group wherein carbon atoms are essential, and it may be a saturated group or an unsaturated group. An atom which can be substituted with fluorine may be a hydrogen atom bonded to carbon.

An atomic group which can be substituted with fluorine may, for example, be a carbon-carbon unsaturated double bond or a carbon-carbon unsaturated triple bond. For example, in a case where a carbon-carbon double bond is present in the organic group, fluorine is added to the carbon-carbon double bond by fluorination in a liquid phase to form a carbon-carbon single bond. Further, in a case where a carbon-carbon triple bond is present in an organic group, fluorine is added to the carbon-carbon triple bond by fluorination in a liquid phase to form a carbon-carbon single bond and a carbon-carbon double bond. Further, a saturated organic group is a group having single bonds alone as the carbon-carbon bonds in the group.

As a monovalent organic group, a group selected from a monovalent hydrocarbon group, a hetero atom-containing monovalent hydrocarbon group, a halogenated monovalent hydrocarbon group and a halogenated (hetero atom-containing monovalent hydrocarbon) group is preferred, and in a case where the monovalent organic group is a saturated group, preferred is a saturated group among the above groups. The organic group has a carbon number of preferably from 1 to 20, particularly preferably from 1 to 10, from the viewpoint of the solubility in a liquid phase used at the time of the fluorination reaction.

The hydrocarbon group may be an aliphatic hydrocarbon group or an aromatic hydrocarbon group, and an aliphatic hydrocarbon group is preferred. Further, in the aliphatic hydrocarbon group, a single bond, a double bond or a triple bond may be present as the carbon-carbon bond. The aliphatic hydrocarbon group may have any of a linear structure, a branched structure, a cyclic structure and a structure having a cyclic structure partially.

The monovalent saturated organic group is preferably a monovalent saturated hydrocarbon group. The monovalent saturated hydrocarbon group may be an alkyl group, and its structure may be any of a linear structure, a branched structure, a cyclic structure and a structure being partially cyclic.

The carbon number of the alkyl group is preferably from 1 to 20, particularly preferably from 1 to 10. The alkyl group having a linear structure may, for example, be a methyl group, an ethyl group, a propyl group or a butyl group. The alkyl group having a branched structure may, for example, be an isopropyl group, an isobutyl group, a sec-butyl group or a tert-butyl group. The alkyl group having a cyclic structure may, for example, be a cycloalkyl group, a bicycloalkyl group or a group having an alicyclic Spiro structure, it is preferably a 3- to 6-membered cycloalkyl group, and a cyclopentyl group or a cyclohexyl group may, for example, be mentioned.

The alkyl group having a cyclic portion may be a (linear structure or branched structure) alkyl group substituted with the above alkyl group having a cyclic structure, or a group having a cyclic group portion in the alkyl group further substituted with a (linear structure or branched structure) alkyl group. Preferred is a group having at least one hydrogen atom in an alkyl group substituted with a 3- to 6-membered cycloalkyl group, and particularly preferred are e.g. a cyclopentylmethyl group, a cyclohexylethyl group and an ethylcyclohexylmethyl group. As another group, an alkyl group having an aromatic ring (for example, an aralkyl group such as a benzyl group or a phenethyl group) or an alkyl group having a heterocyclic ring (for example, a pyridylmethyl group or a furfuryl group) may be mentioned.

A halogen atom in a halogenated group is a fluorine atom, a chlorine atom, a bromine atom or an iodine atom, preferred is a fluorine atom, a chlorine atom or a bromine atom, and particularly preferred is a fluorine atom, or a fluorine atom and a chlorine atom, from the viewpoint of the usefulness of the compound.

In the present specification, halogenation means substitution of at least one hydrogen atom with a halogen atom. Partially halogenation means substitution of a part of hydrogen atoms with halogen atoms. That is, a hydrogen atom is present in a partially halogenated group. Perhalogenation means that all hydrogen atoms are halogenated. That is, no hydrogen atom is present in a perhalogenated group. Such meanings of the terms halogenation, partial halogenation and perhalogenation are similar to the meanings in a case where the halogen atom is specified.

A halogenated saturated hydrocarbon group is a group having at least one hydrogen atom present in the above saturated hydrocarbon group substituted with a halogen atom. A hydrogen atom may or may not be present in the halogenated saturated hydrocarbon group. As the halogen atom in the halogenated saturated hydrocarbon group, a fluorine atom, a chlorine atom, or a fluorine atom and a chlorine atom, are preferred.

A partially halogenated saturated hydrocarbon group is a group having a part of hydrogen atoms present in the above saturated hydrocarbon group substituted with halogen atoms. A hydrogen atom is present in the partially halogenated saturated hydrocarbon group.

A perhalogenated saturated hydrocarbon group is a group having all hydrogen atoms present in the saturated hydrocarbon group substituted with halogen atoms. No hydrogen atom is present in the perhalogenated saturated hydrocarbon group. The halogen atoms present in the halogenated group or the perhalogenated group may be one or at least two kinds.

The halogenated saturated hydrocarbon group may have a linear structure or a branched structure, a cyclic structure or a structure having a cyclic portion. The carbon number of the halogenated saturated hydrocarbon group is preferably from 1 to 20. The halogenated monovalent saturated hydrocarbon group may, for example, be a fluoroalkyl group or a fluoro (partially chlorinated alkyl) group.

A perhalogenated monovalent saturated hydrocarbon group is preferably a perfluoroalkyl group or a perfluoro (partially chlorinated alkyl) group (i.e. a group having all hydrogen atoms in a partially chlorinated alkyl group fluorinated). Further, a perfluoro(partially fluorinated alkyl)

group is the same as a perfluoroalkyl group, and a perfluoro (partially fluorinated alkylene) group is the same as a perfluoroalkylene group.

A hetero atom-containing saturated hydrocarbon group is a group comprising a hetero atom such as an oxygen atom, a nitrogen atom or a sulfur atom, carbon atoms and hydrogen atoms. The hetero atom may be a hetero atom itself or may be a hetero atom group having hetero atoms or a hetero atom and another atom bonded to each other. Each of the hetero atom and the hetero atom group is preferably one unchangeable by pyrolysis reaction. The hetero atom may, for example, be an etheric oxygen atom (O in C—O—C) or =O, and an etheric oxygen atom is particularly preferred. The carbon number of the hetero atom-containing saturated hydrocarbon group is preferably from 1 to 20. As a hetero atom-containing saturated hydrocarbon group, a group having a bivalent hetero atom or a bivalent hetero atom group inserted between a carbon-carbon bond of the above saturated hydrocarbon group, a group having a hetero atom bonded to a carbon atom in the above saturated hydrocarbon group, or a group having a bivalent hetero atom or a bivalent hetero atom group bonded to a carbon atom at the bonding terminal of the above saturated hydrocarbon group is preferred.

As the hetero atom-containing group, an etheric oxygen atom-containing group is particularly preferred in view of usefulness of the compound. Particularly preferred as a monovalent group is an alkyl group containing an etheric oxygen atom (such as an alkoxyalkyl group) from the viewpoint of availability, easiness of production and usefulness of a product. Further, as a monovalent aliphatic hydrocarbon group having a cyclic portion having an etheric oxygen atom inserted between a carbon-carbon atom, an alkyl group having a dioxolane skeleton may, for example, be mentioned.

As the alkoxyalkyl group, preferred is a group having one hydrogen atom present in the alkyl group as mentioned for the above monovalent aliphatic hydrocarbon group substituted with an alkoxy group. The carbon number of the alkoxy group is preferably from 1 to 10. The alkoxyalkyl group may, for example, be an ethoxymethyl group, a 1-propoxyethyl group or a 2-propoxyethyl group.

As the halogenated (hetero atom-containing saturated hydrocarbon) group, a fluoro(hetero atom-containing saturated hydrocarbon) group or a fluoro(partially chlorinated (hetero atom-containing saturated hydrocarbon)) group is preferred. The carbon number of the halogenated (hetero atom-containing saturated hydrocarbon) group is preferably from 1 to 20.

The perhalogenated (hetero atom-containing monovalent saturated hydrocarbon) group may have a linear structure or a branched structure. It is preferably a perfluoro(hetero atom-containing monovalent saturated hydrocarbon) group or a perfluoro(partially chlorinated (hetero atom-containing monovalent saturated hydrocarbon)) group, particularly preferably a perfluoro(hetero atom-containing alkyl) group or a perfluoro(partially chlorinated(hetero atom-containing alkyl)) group, especially preferably a perfluoro(alkoxyl) group or a perfluoro(partially chlorinated (alkoxyl)) group. Specific examples of such groups are shown in specific compounds as described hereinafter.

The ester compound in the present invention is a compound which is an ester of a compound having hydroxyl group(s) with a compound having acyl fluoride group(s) (FC(O)— group), and which has a structure which can be fluorinated. Its preparation method is not particularly limited so long as the ester compound is a compound having a structure formed particularly when a compound having hydroxyl group(s) and a compound having acyl fluoride group(s) are subjected to esterification. For example, as the ester compound, a compound obtained by esterification of a compound having hydroxyl group(s) with at least one compound selected from a ClC(O)— group, a BrC(O)— group and a carboxyl group may be mentioned. Further, the ester compound in the present invention may be a compound obtained by applying another chemical conversion to a portion other than the ester bond after the esterification. The chemical conversion may be a reaction of adding chlorine to a carbon-carbon double bond (C=C) to form a vic-dichloro structure (CCl—CCl). Further, the number of the ester bond in the ester compound is not particularly limited.

The ester compound is preferably a compound produced by esterification of a compound having hydroxyl group(s) with a compound having acyl fluoride group(s). In this case, as the compound having hydroxyl group(s), a compound having at least one hydroxyl group may be employed, and as the compound having acyl fluoride group(s), a compound having at least one acyl fluoride group may be employed.

The ester compound is preferably a compound produced by esterification of a compound having one hydroxyl group with a compound having one acyl fluoride group, and particularly preferably the following compound (3). The compound (3) may be the following compound (3A) wherein $R^1$ is a hydrogen atom, or the following compound (3B) wherein $R^1$ is a monovalent organic group ($R^{10}$):

$$R^A CHR^1 OCOR^{BF} \qquad (3)$$

$$R^A CH_2 OCOR^{BF} \qquad (3A)$$

$$R^A CHR^{10} OCOR^{BF} \qquad (3B)$$

$R^A$ is a monovalent organic group, preferably a group having a hydrogen atom in view of availability of the raw material, more preferably a saturated group having a hydrogen atom from the viewpoint of efficiency of the intended reaction and usefulness of the intended compound.

Further, as $R^A$, a monovalent saturated hydrocarbon group, a partially halogenated monovalent saturated hydrocarbon group, an etheric oxygen atom-containing monovalent saturated hydrocarbon group or a partially halogenated (etheric oxygen atom-containing monovalent saturated hydrocarbon) group is preferred. Particularly preferably, $R^A$ is an alkyl group, a partially chlorinated alkyl group, an alkoxyalkyl group or a partially chlorinated (alkoxyalkyl) group.

$R^A$ is optionally changed depending upon the structure of $R^{AF}$ of the intended compound. One advantage of the method of the present invention is that various structures with different structures of $R^A$ can be employed.

$R^{BF}$ is a perfluoromonovalent organic group, preferably a group having all hydrogen atoms present in a group selected from a monovalent saturated hydrocarbon group, a partially halogenated monovalent saturated hydrocarbon group, an etheric oxygen atom-containing monovalent saturated hydrocarbon group and a partially halogenated (etheric oxygen atom-containing monovalent saturated hydrocarbon) group substituted with fluorine atoms (i.e. a perfluorinated group), particularly preferably a group having all hydrogen atoms present in a group selected from an alkyl group, a partially halogenated alkyl group, an alkoxyalkyl group and a partially halogenated (alkoxyalkyl) group, with fluorine atoms.

$R^1$ is a hydrogen atom or a monovalent organic group. When $R^1$ is a monovalent organic group, preferred is an alkyl group, particularly preferred is a methyl group.

The compound (3) in the present invention preferably has a fluorine content of at least 30 mass %, particularly preferably from 30 to 86 mass %, furthermore preferably from 30 to 76 mass %, from the viewpoint of easiness of a fluorination reaction as described hereinafter, particularly a reaction by using fluorine. If the fluorine content is too low, the solubility in the liquid phase tends to be extremely low, the reaction system of the fluorination reaction tends to be inhomogeneous, and the compound (3) carried out in a continuous reaction may not favorably be fed back to the reaction system. The upper limit of the fluorine content is not limited, however, if it is too high, the compound (3) tends to be difficult to obtain, and the cost tends to increase, such being uneconomical.

The molecular weight of the compound (3) is preferably from 200 to 1000 to prevent an unfavorable fluorination reaction in a gas phase and to carry out a fluorination reaction in a liquid phase smoothly. If the molecular weight is too small, the compound (3) tends to be readily vaporized, whereby a dissociation reaction in a gas phase may take place during the fluorination reaction in a liquid phase. On the other hand, if the molecular weight is too large, it tends to be difficult to purify the compound (3).

The following compounds may be mentioned as specific examples of the compound (3A).

$CH_3(CH_2)_2OCOCF_2CF_3$,
$CH_3(CH_2)_2OCH(CH_3)CH_2OCOCF(CF_3)OCF_2CF_2CF_3$,
$CH_3(CH_2)_2OCH(CH_3)CH_2OCH(CH_3)CH_2OCOCF(CF_3)OCF_2CF(CF_3)O—(CF_2)_2CF_3$,
$CH_2=CHCH(OCH_3)CH_2OCOCF(CF_3)OCF_2CF_2CF_3$,
$CH_2=CHCH_2O(CH_2)_3OCOCF(CF_3)OCF_2CF(CF_3)O(CF_2)_2CF_3$,
$CHCl=CClO(CH_2)_5OCOCF(CF_3)OCF_2CF(CF_3)O(CF_2)_2CF_3$,
$CH_2ClCHClCH_2CH_2OCOCF_2CFClCF_2Cl$.

The following compounds may be mentioned as specific examples of the compound (3B).

$(CH_3)_2CHOCOCF(CF_3)OCF_2CF(CF_3)OCF_2CF_2CF_2$,
$CH_2=CHCH_2CH(CH_3)OCOCF(CF_3)O(CF_2)_2CF_3$.

The compound (3) is preferably a compound produced by esterification of the compound (1) with the compound (2). As the compound (1), the following compound (1A) wherein $R^1$ is a hydrogen atom and the following compound (1B) wherein $R^1$ is a monovalent organic group ($R^{10}$) may be mentioned. Here, $R^A$, $R^1$, $R^{10}$ and $R^{BF}$ are as defined above.

$$R^ACHR^1OH \quad (1)$$

$$FCOR^{BF} \quad (2)$$

$$R^ACH_2OH \quad (1A)$$

$$R^ACHR^{10}OCOR^{BF} \quad (1B)$$

The following compounds may be mentioned as specific examples of the compound (1A).

$CH_3CH_2OH$,
$CH_3CH_2CH_2OH$,
$CH_2=CHCH_2OH$,
$CH_3CH_2CH_2CH_2OH$,
$CH_2ClCHClCH_2CH_2OH$,
$CH_3CH_2CH_2OCH(CH_3)CH_2OH$,
$CH_2=CHCH(OCH_3)CH_2OH$,
$CH_2=CHCH_2OCH_2CH_2CH_2OH$,
$CHCl=CClO(CH_2)_5OH$,
$CF_2ClCFClCH_2CH_2OH$,

The compound (1A) is a compound which is readily available or which can readily be prepared by a known method. For example, 3,4-dichloro-1-butanol can readily be prepared by a known method as disclosed in e.g. U.S. Pat. No. 4,261,901. Further, a 2-alkoxyalcohol can readily be prepared by a known method as disclosed in e.g. J. Am. Chem. Soc., 49, 1080 (1927), Bull. Soc. Chim. Fr., 1813 (1960), Can. J. Chem., 43, 1030 (1965), Synthesis, 280 (1981).

Further, the following compounds may be mentioned as specific examples of the compound (1B).

$CH_2=CHCH_2CH(CH_3)OH$,
$(CH_3)_2CHOH$.

The compound (1) is preferably a compound wherein $R^A$ is a group containing no fluorine atom from the viewpoint of availability. Further, the compound (1) wherein $R^A$ is a group containing fluorine atom, is preferably a compound having a fluorine content of less than 20%, particularly preferably less than 10%.

$R^{BF}$ in the compound (2) is a perfluoromonovalent saturated organic group. The following compounds may be mentioned as specific examples of the compound (2).

$CF_3CF_2COF$,
$CF_3(CF_2)_2COF$,
$CF_2ClCFClCF_2COF$,
$CF_3(CF_2)_2OCF(CF_3)COF$,
$CF_3(CF_2)_2OCF(CF_3)CF_2OCF(CF_3)COF$.

The compound (2) itself is not fluorinated, and it can thereby be used favorably as a liquid solvent to form a liquid phase for the fluorination reaction.

With respect to the method for producing the compound (3) by esterification of the compound (1) with the compound (2), since ones having various structures can be available as the compound (1) having $R^A$ corresponding to $R^{AF}$ of the intended compound (3), compounds (3) with various structures can be produced. Further, by carrying out the fluorination by using the compound (3), the compound (4) which used to be difficult to obtain with a conventional method can be produced. The compound (4) which used to be difficult to obtain by the conventional method, may be one wherein the structure of $R^{AF}$-portion is complex, or a low molecular weight fluorinated ester compound whereby many by-products are formed by a fluorination reaction in a gas phase.

In the present invention, fluorination is carried out in the form of a liquid mixture of the ester compound and the above compound having acyl fluoride group(s). The liquid mixture may be obtained by incorporating an ester compound obtained by various methods into a compound having acyl fluoride group(s). However, the liquid mixture in the present invention is preferably obtained by esterification of a compound having hydroxyl group(s) with a compound having acyl fluoride group(s).

For example, it is preferred that the liquid mixture of an ester compound and a compound having acyl fluoride group(s) is obtained by esterification by using a compound having acyl fluoride group(s), the amount of the compound having acyl fluoride group(s) is larger than the stoichiometric amount which is required to esterify all hydroxyl groups in the compound having hydroxyl group(s), and the amount is such an extent that the unreacted compound having acyl fluoride group(s) remains in the reaction product.

For example, to obtain a liquid mixture of the compound (3) and the compound (2), when the compound (1) and the compound (2) are subjected to esterification, by carrying out the reaction in the presence of the compound (2) in an amount larger than the stoichiometric amount to the compound (1) (hereinafter referred to as "excess amount"), the reaction product may be a liquid mixture of the compound (3) and the compound (2). As the esterification is a reaction which may proceed with a high degree of conversion, when the esterification is carried out by using the compound (2) in an excess amount, substantially all the compound (1) is consumed for the reaction, and the reaction product may be a liquid mixture of the compound (3) which is formed by the esterification and the unreacted compound (2). In this case, the compound (2) is used preferably at least 1.1 times by mol, particularly preferably from 1.1 to 10 times by mol, to the compound (1).

In the method of carrying out the esterification of the compound having acyl fluoride group(s) (such as the compound (2)) in an excess amount with the compound having hydroxyl group(s) (such as the compound (1)), substantially all the compound having hydroxyl group(s) is consumed for the reaction. Thus, there is such an advantage that a step of removing the compound having hydroxyl group(s) in the reaction product can be omitted prior to the following fluorination reaction. Further, there is also such an advantage that conversion of the hydroxyl groups to —OF groups which require careful handling, in the following fluorination reaction, can be prevented. Namely, the method wherein the esterification product of the compound (1) with the compound (2) in an excess amount is a liquid mixture is an advantageous method such that the following fluorination reaction can be carried out without a step of separating the compound (1) after the esterification.

The esterification of the compound (1) with the compound (2) may be carried out in the presence of a solvent other than the compound (2) (hereinafter referred to as solvent 1), however, it is carried out preferably in an excess amount of the compound (2) and in the absence of the solvent 1 from the viewpoint of the operation efficiency. The esterification can adequately proceed even if the solvent 1 is not particularly used, since the excess amount of the compound (2) functions also as a solvent.

Further, HF will be formed by the reaction of the compound (1) with the compound (2), and accordingly an alkali metal fluoride (such as sodium fluoride) may be present in the reaction system as a HF scavenger. The HF scavenger is particularly preferably used in a case where the compound (1) or the compound (2) is unstable to an acid. Further, in a case where no HF scavenger is used, it is preferred to discharge HF out of the reaction system as carried by a nitrogen stream. When an alkali metal fluoride is used, its amount is preferably from 1 to 10 times by mol to the compound (2).

The reaction temperature for the reaction of the compound (1) with the compound (2) is preferably at least −50° C. and at most +100° C. or at most the boiling temperature of the solvent in an ordinary case. Further, the reaction time may suitably be changed depending upon the supply rates of the raw materials and the amounts of the compounds to be used in the reaction. The reaction pressure (gauge pressure, the same applies hereinafter) is preferably from normal pressure to 2 MPa.

In the present invention, fluorination is carried out in the form of a liquid mixture of the ester compound and the compound having acyl fluoride group(s). For example, when the ester compound is the compound (3), the fluorination reaction is carried out in the form of a liquid mixture of the compound (3) and the compound (2). The compound (2) may function as a liquid phase for the fluorination reaction.

Since the compound having acyl fluoride group(s) is a compound having a structure which is similar to or in common with that of the ester compound, it is a compound which can favorably dissolve the ester compound. Particular the compound (2) is a compound wherein $R^{BF}$ is a fluorine-containing group, fluorine can favorably be dissolved in a liquid mixture containing the compound 2 as an essential component. Further, a part of the structure of the compound (2) is similar to or in common with that of the compound (3), and thus the compound (2) is a good solvent for the compound (3).

The compound (2) in the liquid mixture is preferably at least 5 times by mass, particularly preferably from 10 to 100 times by mass to the compound (3). Further, as the compound (2) is consumed in the fluorination reaction, the amount is preferably adjusted to be within the above range by optionally adding the compound (2) in the reaction system of the fluorination reaction.

Further, it is preferred to adjust the structure of $R^{BF}$ in the compound (2) in relation with the structure of $R^A$ in the compound (1), so that the compound (3) is readily dissolved in the liquid phase at the time of fluorination. For example, it is preferred to adjust the structure of $R^{BF}$ so that the fluorine content in the compound (3) will be at least 30 mass %. Further, in a case where $R^1$ is a hydrogen atom as explained hereinafter, it is particularly preferred to select $R^{BF}$ to be the same as $R^{AF}$, since the step of separating the reaction product can be simplified.

When the liquid mixture is prepared by the esterification, the reaction crude product of the esterification may be directly used, or may be subjected to work-up process as the case requires. The work-up process of the crude product may, for example, be a method of directly distilling the crude product, a method of treating the crude product with a diluted alkali aqueous solution, followed by liquid separation, a method of extracting the crude product with a suitable organic solvent, followed by distillation, or silica gel column chromatography. In a case where the compound having hydroxyl group(s) (such as the compound (1)) is contained in the crude product, it is preferred to remove the compound (1) as far as possible. The compound having hydroxyl group(s) is preferably at most 10%, particularly preferably at most 3%, especially preferably at most 1%, in the liquid phase.

The fluorination reaction in the present invention is a reaction wherein at least one fluorine atom is introduced to the ester compound. The fluorination reaction is carried out as a liquid phase reaction. The fluorination reaction may be an ECF method, a cobalt fluorination method or a method of reaction with fluorine ($F_2$). Among them, a method of reaction with fluorine in a liquid phase (hereinafter referred to as liquid phase fluorination method) is preferred, which provides a high yield and in which fluorination of the ester compound proceeds advantageously.

As the fluorine in the liquid phase fluorination method, fluorine gas may be directly used, or fluorine gas diluted with an inert gas may be used. As the inert gas, nitrogen gas or helium gas is preferred, and nitrogen gas is particularly preferred from economical reasons. The amount of fluorine gas in the nitrogen gas is not particularly limited, but it is preferably at least 10 vol %, from the viewpoint of efficiency, particularly preferably at least 20 vol %.

As the liquid phase of the liquid phase fluorination reaction, a compound having acyl fluoride group(s) is essential. In the fluorination of the compound (3), the compound (2) is essential as the liquid phase. Further, the compound (3) as a substrate of the fluorination reaction or the compound (4) to be formed in the fluorination reaction may also be used as a liquid phase. Further, as the liquid phase of the liquid phase fluorination reaction, a solvent other than the compound (2), compound (3) and compound (4) (hereinafter referred to as the solvent 2) may be contained, however, no solvent 2 is preferably used in order to obtain the effect of the present invention to the fullest extent.

The reaction system for the liquid phase fluorination reaction is preferably a batch system or a continuous system. Further, the liquid phase fluorination reaction of the compound (3) is preferably carried out by the following fluorination method 1 or fluorination method 2, and the fluorination method 2 is preferred from the viewpoint of the reaction yield and the selectivity. Further, as the fluorine gas, one diluted with an inert gas such as nitrogen gas may be used either in the case of the batch system or in the case of the continuous system.

Fluorination method 1 A liquid mixture of the compound (3) and the compound (2) is charged to a reactor, and stirring is initiated. Then, the reaction is carried out while continuously supplying fluorine gas to the liquid phase in the reactor at a prescribed reaction temperature and reaction pressure.

Fluorination method 2 The compound (2) is charged to a reactor, and stirring is initiated. Then, the liquid mixture of the compound (3) and the compound (2) and fluorine gas are continuously and simultaneously supplied to the liquid phase in the reactor at a prescribed molar ratio at a prescribed reaction temperature and reaction pressure.

As the liquid mixture of the compound (3) and the compound (2) in the fluorination method 2, the reaction product obtained by reacting the compound (1) with an excess amount of the compound (2) may be directly used, or one having the compound (2) further added as the case requires may be used. Further, when the compound (3) is diluted in the fluorination method 2, the concentration of the compound (3) is preferably at most 20 mass %, particularly preferably at most 10 mass %.

With respect to the fluorine amount used for the fluorination reaction, it is preferred to carry out the reaction in a state where fluorine is present so that the fluorine amount is always in an excess equivalent amount to hydrogen atoms in the ester compound, either in the case of carrying out the reaction by a batch system or in the case of carrying out the reaction by a continuous system, and it is particularly preferred to use fluorine in an amount of at least 1.5 times by equivalent (i.e. at least 1.5 times by mol) from the viewpoint of selectivity. Further, it is preferred to keep the fluorine amount to be always in an excess equivalent amount from the initiation of the reaction to the completion.

The reaction temperature for the fluorination reaction is usually preferably at least −60° C. and at most the boiling point of the ester compound, particularly preferably from −50° C. to +100° C. from the viewpoint of the reaction yield, selectivity and industrial applicability, especially preferably from −20° C. to +50° C. The reaction pressure for the fluorination reaction is not particularly limited, and it is particularly preferably from 0 to 20 MPa from the viewpoint of the reaction yield, selectivity and industrial applicability.

Further, in order to let the fluorination reaction proceed efficiently, it is preferred to add a C—H bond-containing compound to the reaction system, or to carry out ultraviolet irradiation. When such an operation is carried out, the ester compound present in the reaction system can efficiently be fluorinated, and the conversion can remarkably be improved.

The C—H bond-containing compound is preferably an organic compound other than the ester compound, it is particularly preferably an aromatic hydrocarbon, especially preferably benzene, toluene or the like. The amount of the C—H bond-containing compound is preferably from 0.1 to 10 mol %, to the hydrogen atoms in the ester compound, particularly preferably from 0.1 to 5 mol %. Further, when the C—H bond-containing compound is diluted with a solvent and then added, it is preferred that the solvent for the dilution is also a compound having acyl fluoride group(s) (such as the compound (2)).

The C—H bond-containing compound is added preferably in such a state that fluorine gas is present in the reaction system. Further, in a case where the C—H bond-containing compound is added, it is preferred to pressurize the reaction system. The pressure for pressurizing is preferably from 0.01 to 5 MPa.

If a hydrogen atom is substituted with a fluorine atom in the fluorination reaction, HF will be formed as a by-product. To remove the by-product HF, it is preferred to let a HF scavenger coexist in the reaction system or to let a discharge gas contact with a HF scavenger at a gas outlet of the reactor. As such a HF scavenger, the same ones as mentioned above may be employed, and NaF is preferred.

In a case where a HF scavenger is permitted to coexist in the reaction system, its amount is preferably from 1 to 20 times by mol, particularly preferably from 1 to 5 times by mol to the total amount of hydrogen atoms present in the ester compound. In a case where the HF scavenger is placed at the gas outlet of the reactor, it is advisable to arrange (a) a cooler (preferably to maintain the temperature at from 10° C. to room temperature, particularly preferably at about 20° C.), (b) a packed layer of NaF pellets and (c) a cooler (preferably to maintain the temperature from −78° C. to +10° C., preferably from −30° C. to 0° C.) in series in the order of (a)-(b)-(c). Further, a liquid returning line to return the condensed liquid from the cooler (c) to the reactor, may be provided.

In the fluorination of the present invention, a fluorinated ester compound will be formed. In the fluorination reaction, a fluorinated ester compound having a structure corresponding to the carbon skeleton of the ester compound will be formed. Here, in a case where a carbon-carbon unsaturated bond is present in the ester compound, fluorine atoms may be added to at least one unsaturated bond to change the bond state. For example, by fluorination of the compound (3), the compound (4) is formed. The compound (4) is a compound wherein at least one fluorine atom is introduced to the molecule of the compound (3).

$R^{AF}$ in the compound (4) is a group corresponding to $R^A$. $R^{AF}$ in a case where $R^A$ is a hydrogen atom which can be fluorinated or a monovalent organic group having an unsaturated bond and said group is fluorinated, is a group obtained by fluorination of $R^A$. Further, in a case where $R^A$ is a monovalent organic group which can not be fluorinated or in a case where it is not fluorinated even if it is a group which can be fluorinated, it is the same group as $R^A$. In $R^{AF}$ and $R^A$, there is no change in the arrangement of carbon atoms as before and after the fluorination reaction. Further, $R^{BF}$ is the same group as $R^{BF}$ in the compound (3). $R^{1F}$ is a fluorine atom when $R^1$ is a hydrogen atom. When $R^1$ is a monovalent organic group, $R^{1F}$ is a monovalent organic group which may be the same as or different from $R^1$, and when $R^1$ and $R^{1F}$ are different from each other, $R^{1F}$ is a monovalent organic group obtained by fluorination of $R^1$.

The fluorinated ester compound is preferably a compound obtained by perfluorination of an ester compound. Since $R^A$ in the compound (3) is preferably a hydrogen-containing group in view of availability of the compound, $R^{AF}$ in the compound (4) is preferably a fluorinated group, particularly preferably a perfluorinated group.

The compound (4) may be the following compound (4A) or the following compound (4B). Here, $R^{AF}$ and $R^{BF}$ are as defined above.

$$R^{AF}CFR^{1F}OCOR^{BF} \qquad (4)$$

$$R^{AF}CF_2OCOR^{BF} \qquad (4A)$$

$$R^{AF}CFR^{10F}OCOR^{BF} \qquad (4B)$$

Further, $R^{AF}$ is preferably a group having all hydrogen atoms present in $R^A$ substituted with fluorine atoms, $R^A$ being a monovalent saturated hydrocarbon group, a partially halogenated monovalent saturated hydrocarbon group, an etheric oxygen atom-containing monovalent saturated hydrocarbon group, or a partially halogenated (etheric oxygen atom-containing monovalent saturated hydrocarbon) group. Particularly preferably $R^{AF}$ is a group having all hydrogen atoms present in $R^A$ substituted with fluorine atoms, $R^A$ being an alkyl group, a partially chlorinated alkyl group, an alkoxyalkyl group or a partially chlorinated (alkoxyalkyl) group.

$R^{10F}$ in the compound (4B) is a monovalent organic group which may be the same as or different from $R^{10}$, and when they are different from each other, it is a monovalent organic group obtained by fluorination of $R^{10}$. $R^{10F}$ is preferably a monovalent organic group obtained by perfluorination of $R^{10}$, particularly preferably a perfluoroalkyl group, especially preferably a trifluoromethyl group from the viewpoint of usefulness of the compound.

The following compounds may be mentioned as specific examples of the compound (4A).

CF$_3$(CF$_2$)$_2$OCOCF$_2$CF$_3$,
CF$_3$(CF$_2$)$_2$OCF(CF$_3$)CF$_2$OCOCF(CF$_3$)OCF$_2$CF$_2$CF$_3$,
CF$_3$(CF$_2$)$_2$OCF(CF$_3$)CF$_2$OCF(CF$_3$)CF$_2$OCOCF(CF$_3$)OCF$_2$CF(CF$_3$)O(CF$_2$)$_2$CF$_3$,
CF$_3$CF$_2$CF(OCF$_3$)CF$_2$OCOCF(CF$_3$)OCF$_2$CF$_2$CF$_3$,
CF$_3$CF$_2$CF$_2$O(CF$_2$)$_3$OCOCF(CF$_3$)OCF$_2$CF(CF$_3$)O(CF$_2$)$_2$CF$_3$,
CF$_2$ClCFClO(CF$_2$)$_5$OCOCF(CF$_3$)OCF$_2$CF(CF$_3$)O(CF$_2$)$_2$CF$_3$,
CF$_2$ClCFClCF$_2$CF$_2$OCOCF$_2$CFClCF$_2$Cl.

The following compounds may be mentioned as specific examples of the compound (4B).

(CF$_3$)$_2$CFOCOCF(CF$_3$)OCF$_2$CF(CF$_3$)OCF$_2$CF$_2$CF$_3$,
CF$_3$CF$_2$CF$_2$CF(CF$_3$)OCOCF(CF$_3$)O(CF$_2$)$_2$CF$_3$.

The fluorinated ester compound as a reaction product of the fluorination reaction is useful as it is or as chemically converted to another compound. When the fluorinated ester compound is a compound having a dissociatable ester bond, particularly when it is the compound (4), it may be introduced to another compound by carrying out a dissociation reaction of the ester bond.

Here, the product of the fluorination reaction includes a fluorinated ester compound. Further, in a case where the fluorination reaction is carried out in the presence of a compound having acyl fluoride group(s), the product of the fluorination reaction includes, in a case where the compound having acyl fluoride group(s) is a compound which is not fluorinated, the same compound as said compound, and in a case where the compound having acyl fluoride group(s) is fluorinated, the fluorinated compound having acyl fluoride group(s). Further, in a case where the HF scavenger or the solvent 2 is employed, they may be present in the reaction product.

When a dissociation reaction of the ester bond is carried out on the fluorinated ester compound, the fluorinated ester compound may be purified and taken out from the reaction product of the fluorination reaction, or the reaction product may directly be employed for the following ester bond dissociation reaction, and it is particularly preferred to carry out the dissociation reaction of the ester bond by the latter method. In the case of purification, a method of directly distilling the crude product under normal pressure or under reduced pressure may, for example, be mentioned.

In a case where the dissociation reaction of the ester bond is carried out on the compound (4), the following compound (5) and the above compound (2) will be formed. The compound (5) may be a compound (5A) and a compound (5B). Here, $R^{AF}$, $R^{1F}$ and $R^{10F}$ are as defined above.

$$R^{AF}COR^{1F} \qquad (5)$$

$$R^{AF}COF \qquad (5A)$$

$$R^{AF}COR^{10F} \qquad (5B)$$

The compound (5B) which is a fluorine-containing ketone, itself is a useful compound as e.g. a solvent. Further, it may be converted to a fluorine-containing alcohol by a reduction reaction. Further, the compound (5A) is a useful compound as a material of a fluororesin monomer or a fluorine-containing alcohol.

The following compounds may be mentioned as specific examples of the compound (5A).

CF$_3$CF$_2$COF,
CF$_3$(CF$_2$)$_2$COF,
CF$_2$ClCFClCF$_2$COF,
CF$_3$CF$_2$CF$_2$OCF(CF$_3$)COF,
CF$_3$CF$_2$CF$_2$OCF(CF$_3$)CF$_2$OCF(CF$_3$)COF,
CF$_3$(CF$_2$)$_2$OCF(CF$_3$)CF$_2$OCF(CF$_3$)COF,
CF$_2$ClCFClO(CF$_2$)$_4$COF.

Further, the following compounds may be mentioned as specific examples of the compound (5B).

(CF$_3$)$_2$C(O),
CF$_3$CF$_2$CF$_2$C(O)(CF$_3$).

The dissociation reaction of the ester bond is preferably carried out by dissociation of the ester bond by heating, or by dissociation of the ester bond in the presence of a nucleophilic agent or an electrophilic agent.

In a case where the ester bond is dissociated by heating (hereinafter referred to as pyrolysis), it is advisable to select the type for the pyrolysis depending upon the boiling point and stability of the fluorinated ester compound. For example, in a case where a volatile fluorinated ester compound is pyrolyzed, a gas phase pyrolysis may be adopted wherein it is continuously pyrolyzed in a gas phase, and the outlet gas containing the product is condensed and recovered.

The reaction temperature for the gas phase pyrolysis is preferably from 50 to 350° C., particularly preferably from 50 to 300° C., especially preferably from 150 to 250° C. Further, an inert gas which will not be involved directly in the reaction, may be present in the reaction system. As such an inert gas, nitrogen gas or carbon dioxide gas may, for example, be mentioned. It is preferred that the inert gas is added in an amount of from about 0.01 to 50 vol %, based on the fluorinated ester compound. If the amount of the inert gas is large, the recovered amount of the product may decrease.

Further, in the gas phase pyrolysis, it is preferred to employ a tubular reactor. In a case where a tubular reactor is used, the retention time is preferably from about 0.1 second to about 10 minutes on the basis of a vacant column standard. The reaction pressure is not particularly limited. Further, in a case where the fluorinated ester compound is a high boiling point compound, it is preferred to carry out the reaction under reduced pressure. Particularly when the fluorinated ester compound is a low boiling point compound, it is preferred to carry out the reaction under a pressurized condition so that decomposition of the product will be suppressed and the rate of reaction will increase.

In a case where the gas phase reaction is carried out by using a tubular reactor, it is preferred to fill the reaction tube with glass, an alkali metal salt or an alkaline earth metal salt with a purpose of accelerating the reaction. In a case where the dissociation reaction of the ester bond is carried out in the form of a mixture of the fluorinated ester compound and a compound having acyl fluoride group(s) or a fluoride of said compound, such a filler is preferably selected from ones which do not accelerate the decomposition reaction of the compound having acyl fluoride group(s).

The alkali metal salt or the alkaline earth metal salt is preferably a carbonate or a fluoride. As the glass, general soda glass may be mentioned, and bead-like glass beads having an increased fluidity are particularly preferred. The alkali metal salt may be sodium carbonate, sodium fluoride, potassium carbonate or lithium carbonate. The alkaline earth metal salt may, for example, be calcium carbonate, calcium fluoride or magnesium carbonate. Further, when the reaction tube is filled with glass, an alkali metal salt or an alkaline earth metal salt, it is particularly preferred to use glass beads or light ash of sodium carbonate having a particle size of from about 100 to about 250 μm, whereby a fluidized bed type reaction system can be employed.

On the other hand, in a case where the fluorinated ester compound is a hardly volatile compound, it is advisable to employ a liquid phase pyrolysis wherein it is heated in the state of a liquid in the reactor. In such a case, the reaction pressure is not particularly limited. In a usual case, the product of the ester bond dissociation reaction has a lower boiling point than that of the fluorinated ester compound, and accordingly, it is preferred to obtain it by a method by a reaction distillation system wherein the product is vaporized and continuously withdrawn. Otherwise, a method may be employed wherein after completion of the heating, the product is withdrawn all at once from the reactor. The reaction temperature for this liquid phase pyrolysis is preferably from 50 to 300° C., particularly preferably from 100 to 250° C.

In a case where the dissociation reaction of the ester bond is carried out by the liquid phase pyrolysis, it is preferred to carry out the reaction by using the reaction product of the fluorination reaction directly from the viewpoint of operation efficiency. To the reaction product, a solvent may be added, however, it is preferred to add no solvent. For example, in the fluorination reaction of a liquid mixture of the compound (2) and the compound (3), the compound (2) and the compound (4) are contained in the product, and it is preferred that the dissociation reaction of the ester bond is carried out in the form of the mixture of the compound (2) and the compound (4), and that no solvent other than the compound (2) (hereinafter referred to as solvent 3) is present. In this case, the compound (2) may optionally be added. The compound (2) may also act as a liquid phase in the dissociation reaction of the ester bond.

Further, when the compound (4) itself is a liquid, the dissociation reaction of the ester bond may be carried out in the absence of any solvent. The method carried out in the absence of any solvent is preferred from the viewpoint of the volume efficiency and suppression of by-products. On the other hand, in a case where the solvent 3 is used, it is preferred to select one which does not react with the compound (4) and is compatible with the compound (4), and which does not react with the product.

As a specific example of the solvent 3, preferred is an inert solvent such as a perfluorotrialkylamine, or a chlorofluorocarbon, specifically a chlorotrifluoroethylene oligomer having a high boiling point (for example, tradename: FLON LUBE).

Further, in a case where the dissociation reaction of the ester bond is carried out by reacting the fluorinated ester compound with a nucleophilic agent or an electrophilic agent in a liquid phase, such a reaction may be carried out in the presence or absence of a solvent. In a case where the reaction of the compound (4) is carried out in the presence of a solvent, it is preferred to carry out the reaction in the presence of the compound (2). As the nucleophilic agent, F$^-$ is preferred, and particularly preferred is F$^-$ derived from an alkali metal fluoride. As the alkali metal fluoride, NaF, NaHF$_2$, KF or CsF may be used, and among them, NaF is particularly preferred from the viewpoint of the economical efficiency, and KF is particularly preferred from the viewpoint of the reaction efficiency.

In a case where the dissociation reaction of the ester bond is carried out by a method of reacting the compound (4) with a nucleophilic agent (such as F$^-$), F$^-$ will be nucleophilically added to the carbonyl group present in the ester bond in the compound (4), whereby R$^{AF}$CFR$^{1F}$O$^-$ will be detached, and the compound (2) will be formed. Further, F$^-$ will be detached from R$^{AF}$CFR$^{1F}$O$^-$ to form the compound (5). Depending upon the conditions of the dissociation reaction, the compound (4) may further decompose to form another compound (such as an unsaturated compound). The detached F$^-$ will react with another compound (4) in a similar manner. Accordingly, the nucleophilic agent initially employed for the reaction may be in a catalytic amount or in an excess amount. Namely, the amount of the nucleophilic agent such as F$^-$ is preferably from 1 to 500 mol %, particularly preferably from 10 to 100 mol %, especially preferably from 5 to 50 mol %, based on the compound (4). The reaction temperature is preferably from −30° C. to the boiling point of the solvent or the compound (4), particularly preferably from −20° C. to 250° C. This method is also preferably carried out in a reaction distillation system.

In a case where the fluorinated ester compound is the compound (4A), under an usual condition, the compound (2) together with the compound (5A) is contained in the reaction product of the ester dissociation reaction. Further, in a case where the dissociation reaction of the ester bond is carried out in the presence of the compound (2), the compound (2) is contained in the reaction product.

The compound (5A) and the compound (2) in the reaction product can readily be separated by a usual separation method. However, in a case where the raw material compounds are selected so that the compound (5A) has the same structure as the compound (2), i.e. in a case where the structure of the groups is selected so that R$^{AF}$ and R$^{BF}$ have the same structure in the compound (4A), the compound (5) and the compound (2) as the reaction products are the same compound, whereby an operation to separate the reaction products can be omitted.

As a preferred embodiment of the present invention, a method may be mentioned wherein the structure of the groups is selected so that R$^{AF}$ and R$^{BF}$ have the same structure, the compound (3A) is fluorinated in a liquid phase which has an excess amount of the compound (2) as an essential component, and a mixture of the compound (4A) formed by the fluorination and the compound (2) is introduced to the following dissociation reaction of the ester bond. In this method, the compound (5A) as a product of the dissociation reaction of the ester bond is the same compound as the compound (2), and a step of separating and purifying the product can be simplified. Further, also in a case where a solvent is used for each reaction, by employing the compound (2) alone as the solvent, the type of the solvent used can be decreased, whereby work-up process can be omitted.

Further, as another preferred embodiment, a method may be mentioned wherein when the compound (1) and the compound (2) are subjected to esterification, the reaction is carried out in the presence of an excess amount of the compound (2) to obtain a liquid mixture of the compound (3) and the compound (2), which is used for the fluorination reaction. By this method, an operation to remove the compound (1) prior to the fluorination reaction can also be omitted. Further, a method may be mentioned wherein the reaction to dissociate the ester bond is carried out in the form of a mixture of the compound (4) formed by the fluorination reaction and the compound (2). Such a series of the reactions may be carried out in one reactor.

Further, as still another preferred embodiment, a method may be mentioned wherein the compound (5A) or the compound (2) obtained from the product of the dissociation reaction of the ester bond is recycled as the compound (2) to be reacted with the compound (1). This method is a method which enables to continuously produce the compound (5A). Namely, the compound (2) is obtained from the reaction product of the dissociation reaction of the ester bond by using the liquid mixture of the compound (4A) and the compound (2), and a part or whole of the compound (2) is used for the reaction with the compound (1A) again, whereby the compound (5A) can be continuously produced. This method is a method which enables to continuously produce the desired compound (5A) from the raw material compound (1A) which is available at a low cost.

EXAMPLES

Now, the present invention will specifically be explained with reference to Examples, however, the present invention is by no means restricted thereto. In the following, gas chromatography is represented by GC, gas chromatography mass spectrometry is represented by GC-MS, and milliliter is represented by mL. NMR spectrum data are shown within the apparent chemical shift range. The standard value for the standard substance $CDCl_3$ in $^{13}C$-NMR was set to be 76.9 ppm. For the quantitative analysis by $^{19}F$-NMR, $C_6F_6$ was used as the internal standard sample.

Example 1

Example 1-1

Example for Preparation of a Liquid Mixture of $CF_3CF_2CF_2OCF(CF_3)COOCH_2CH(CH_3)OCH_2CH_2CH_3$ and $CF_3CF_2CF_2OCF(CF_3)COF$ $CH_3CH_2CH_2OCH(CH_3)CH_2OH$ (620.1 g) was put into a flask and stirred while bubbling nitrogen gas. While maintaining the internal temperature at from 25 to 35° C., $CF_3CF_2CF_2OCF(CF3)COF$ (3604 g) was dropwise added thereto over a period of 8 hours. After completion of the dropwise addition, stirring was carried out at room temperature for 2 hours while bubbling nitrogen gas to the reaction product containing $CF_3CF_2CF_2OCF(CF_3)COOCH_2CH(CH_3)OCH_2CH_2CH_3$ and $CF_3CF_2CF_2OCF(CF_3)COF$ to obtain the above-identified liquid mixture. The liquid mixture was directly used for the reaction of Example 1-2.

Example 1-2

Example for Preparation of $CF_3CF_2CF_2OCF(CF_3)COOCF_2CF(CF_3)OCF_2CF_2CF_3$

Into a 3 L autoclave made of nickel, $CF_3CF_2CF_2OCF(CF_3)COF$ (2340 g) was added, stirred and maintained at 25° C. At the gas outlet of the autoclave, a cooler maintained at 20° C., a packed layer of NaF pellets and a cooler maintained at −10° C. were installed in series. Further, a liquid returning line was installed to return a liquid condensed from the cooler maintained at −10° C. to the autoclave. After supplying nitrogen gas for 1.5 hours, fluorine gas diluted to 20 vol % with nitrogen gas (hereinafter referred to as 20% fluorine gas) was supplied at a flow rate of 8.91 L/h for 3 hours.

Then, while supplying 20% fluorine gas at the same flow rate, 18 mL of the liquid mixture (106 g) obtained in Example 1-1 was injected over a period of 45.6 hours.

Then, while supplying 20% fluorine gas at the same flow rate, a $CF_3CF_2CF_2OCF(CF_3)COF$ solution having a benzene concentration of 0.01 g/mL was injected while raising the temperature from 25° C. to 40° C., the benzene injection inlet of the autoclave was closed, the outlet valve of the autoclave was closed, and when the pressure became 0.20 MPa, the fluorine gas inlet valve of the autoclave was closed, and stirring was continued for 1 hour. Then, the pressure was returned to normal pressure, and while maintaining the internal temperature of the reactor at 40° C., 6 mL of the above benzene solution was injected, the benzene injection inlet of the autoclave was closed, the outlet valve of the autoclave was closed, and when the pressure became 0.20 MPa, the fluorine gas inlet valve of the autoclave was closed, and stirring was continued for 1 hour. The same operation was repeated once.

The total amount of benzene injected was 0.309 g, and the total amount of $CF_3CF_2CF_2OCF(CF_3)COF$ injected was 30 mL. Further, nitrogen gas was supplied for 2.0 hours. After the reaction, purification by distillation was carried out to obtain a reaction product containing the above-identified compound (85.3 g) and $CF_3CF_2CF_2OCF(CF_3)COF$. The results of analysis of the above-identified compound in the reaction product are shown below.

Boiling point: 46–51° C./5.2 kPa.

High resolution mass spectrum (CI method) 664.9496 (M+H. theoretical value: $C_{12}HF_{24}O_4$=664.9492).

$^{19}F$-NMR(564.6 MHz solvent $CDCl_3/C_6F_6$, standard: $CFCl_3$) δ (ppm): −80.6(1F), −80.8 and −80.9(3F), −81.6−−83.1(2F), −82.6(6F) −82.8(3F), −86.7(1F), −87.4(1F), −87.5(1F), −130.6(4F), −132.2(1F), −145.7 and −145.9(1F).

$^{13}C$-NMR(150.8 MHz, solvent $CDCl_3/C_6F_6$, standard: $CDCl_3$) δ (ppm): 100.26 and 100.28, 102.8, 106.8, 107.0, 116.0, 116.2, 116.5 and 1 16.6, 117.4, 117.5, 117.9, 117.9, 152.2 and 152.3.

Example 1-3

Example for Preparation of $CF_3CF_2CF_2OCF(CF_3)COF$

The reaction product containing $CF_3CF_2CF_2OCF(CF_3)COOCF_2CF(CF_3)OCF_2CF_2CF_3$ (83.0 g) obtained in Example 1-2 was charged together with NaF powder (1.1 g) into a flask and heated at 140° C. for 15 hours in an oil bath, while vigorously stirring. At an upper portion of the flask, a liquid sample (81.3 g) was recovered through a reflux condenser having the temperature adjusted to 70° C. A product obtained by distilling the liquid sample for purification was analyzed by GC-MS, whereupon formation of $CF_3CF_2CF_2OCF(CF_3)COF$ was confirmed.

Example 1-4

Example for Continuous Preparation of $CF_3CF_2CF_2OCF(CF_3)COF$

By using $CF_3CF_2CF_2OCF(CF_3)COF$ (81.2 g) obtained by the method of Example 1-3 and $CH_3CH_2CH_2OCH(CH_3)CH_2OH$ (14.0 g), they are reacted in the same manner as in Example 1-1 to obtain a liquid mixture (94.0 g) containing $CF_3CF_2CF_2OCF(CF_3)COOCH_2CH(CH_3)OCH_2CH_2CH_3$ and $CF_3CF_2CF_2OCF(CF_3)COF$. By using the liquid mixture, the same reactions as in Examples 1-2 and 1-3 were carried out to obtain the above-identified compound.

Example 2

Example 2-1

Example for Preparation of $CH_2$=$CHCH(OCH_3)CH_2OCOCF(CF_3)OCF_2CF_2CF_3$ $CH_2$=$CHCH(OCH_3)CH_2OH$ (270 g) was charged together with NaF (334 g) into a 2 L pressure resistant reactor equipped with a reflux condenser in which a coolant at 20° C. circulated, and stirred at –10° C. While discharging by-product HF formed by the reaction out of the system from the reflux condenser on the upper portion by bubbling nitrogen gas to the reactor, $FCOCF(CF_3)OCF_2CF_2CF_3$ (1055 g) was dropwise added over a period of 1.5 hours. At this time, the temperature was adjusted so that the internal temperature of the reactor would be at most 0° C. After completion of the dropwise addition, stirring was carried out at 30° C. for 18 hours and then the reaction was terminated.

NaF contained in the crude liquid after completion of the reaction was collected by filtration to obtain a crude product (981 g) (yield 86.4%). As a result of the analysis by NMR, the above-identified mixture was obtained as a liquid mixture with $FCOCF(CF_3)OCF_2CF_2CF_3$. The results of analysis of the above-identified compound are as follows.

$^1$H-NMR(300.4 MHz, solvent:CDCl$_3$, standard:TMS) δ (ppm): 3.29(s, 3H), 3.85–3.90(m, 1H), 4.24–4.45(m, 2H), 5.34(s, 1H), 5.39(d,J=8.4 Hz, 1H), 5.59–5.71(m, 1H).

$^{19}$F-NMR(282.7 MHz, solvent:CDCl$_3$, standard:CFCl$_3$) δ (ppm): –81. 8(3F), –82.6(3F), –79.9--–87.5(2F), –130.2 (2F), –132.3(1F).

Example 2-2

Example for Preparation of a Liquid Mixture of $CH_2ClCHClCH(OCH_3)CH_2OCOCF(CF_3)OCF_2CF_2CF_3$ and $FCOCF(CF_3)OCF_2CF_2CF_3$ The liquid mixture containing $CH_2$=$CHCH(OCH_3)CH_2OCOCF(CF_3)OCF_2CF_2CF_3$ (981 g) obtained by the method of Example 2-1 was charged into a 2 L three-necked flask equipped with a dimroth cooled at 0° C., and while carrying out stirring at from –10 to 0° C., chlorine gas was introduced at a rate of 0.8 g/min to carry out the reaction. The reaction was terminated when 170 g of chlorine gas was introduced, and 1084 g of a crude liquid was obtained.

The obtained crude liquid was distilled off under a reduced pressure of from 6 to 7 mmHg for purification to obtain 744 g of a product. As a result of analysis by NMR and gas chromatography, formation of a liquid mixture containing $CH_2ClCHClCH(OCH_3)CH_2OCOCF(CF_3)OCF_2CF_2CF_3$ and $FCOCF(CF_3)OCF_2CF_2CF_3$ with a GC purity of 98% was confirmed. The results of analysis of $CH_2ClCHClCH(OCH_3)CH_2OCOCF(CF_3)OCF_2CF_2CF_3$ and $FCOCF(CF_3)OCF_2CF_2CF_3$ are as follows.

$^1$H-NMR(300.4 MHz, solvent:CDCl$_3$, standard:TMS) δ (ppm): 3.45(d, J=1.5 Hz) and 3.47(s) and 3.55(d J=0.6 Hz) total 3H, 3.56–3.80(m, 2H), 3.82–4.12(m, 2H), 4.43–4.57 (m, 1H), 4.65(dd,J=6.3 Hz, 11.4 Hz) and 4.89(ddd,J=42.4 Hz, 12.0 Hz, 3.0 Hz) and 5.49(q,J=5.1 Hz) total 1H.

$^{19}$F-NMR(376.0 MHz, solvent:CDCl$_3$, standard:CFCl$_3$) δ (ppm): –79. 93--–80.65(1F), –81.72--–81.80(3F), –82.47-- 82.56(3F), –86.46--–87.22(1F), –130.07--–130.19(2F), –132.26--–132.47(1F)

Example 2-3

Example for Preparation of $CF_2ClCFClCF(OCF_3)CF_2OCOCF(CF_3)OCF_2CF_2CF_3$ Into a 3 L autoclave made of nickel, $CF_3CF_2CF_2OCF(CF_3)COF$ (3523 g) was added and stirred, and maintained at 5° C. At the gas outlet of the autoclave, a cooler maintained at –10° C. was installed. After supplying nitrogen gas for 3.5 hours, 20% fluorine gas was supplied at a flow rate of 26.52 L/h for 1 hour.

Then, while supplying 20% fluorine gas at the same flow rate, the liquid mixture containing $CH_2ClCHClCH(OCH_3)CH_2OCOCF(CF_3)OCF_2CF_2CF_3$ (415 g) obtained by the method of Examples 2-1 and 2-2 was injected over a period of 22.5 hours, and then the reaction crude liquid (261 g) was withdrawn (operation 1). Operations 2 to 3 as identified in the following Table were carried out in the same manner. Then, the temperature in the autoclave was brought to 25° C. and maintained for 22 hours, and then the supply of fluorine gas was stopped, nitrogen gas was supplied for 3.0 hours, and the reaction crude liquid (3530 g) was withdrawn.

The reaction crude liquids were put together and analyzed by GC-MS and as a result, a mixture containing $CF_3CF_2CF_2OCF(CF_3)COF$ and the above-identified compound as the main components was confirmed, and the yield of the above-identified compound (1A) was 71%.

TABLE 1

| Operation | Amount injected (g) | Injection time (hr) | Reaction crude liquid |
|---|---|---|---|
| 1 | 415 | 22.5 | 261 |
| 2 | 642 | 22.0 | 533 |
| 3 | 471 | 22.8 | 270 |

Example 3

Example 3-1

Example for Preparation of a Liquid Mixture of $(CH_3)_2CHOCOCF(CF_3)OCF_2CF(CF_3)OCF_2CF_2CF_3$ and $FCOCF(CF_3)OCF_2CF(CF_3)OCF_2CF_2CF_3$ $(CH_3)_2CHOH$ (7.0 kg) was put in a reactor, followed by stirring while bubbling nitrogen gas. $FCOCF(CF_3)OCF_2CF$ $(CF_3)OCF_2CF_2CF_3$ (61.0 kg) was added thereto over a period of 25 hours while maintaining the internal temperature of the reactor at from 25 to 30° C. After completion of the addition, stirring was carried out for 24 hours while maintaining the internal temperature of the reactor at 30° C., to obtain 65.1 kg of the above-identified liquid mixture as a crude liquid. The purity of $(CH_3)_2CHOCOCF(CF_3)OCF_2CF(CF_3)OCF_2CF_2CF_3$ was 98% as measured by GC.

Example 3-2

Example for Prepration of $(CF_3)_2CFOCOCF(CF_3)OCF_2CF(CF_3)OCF_2CF_2CF_3$

Into a 4 L autoclave made of nickel, $CF_3CF_2CF_2OCF(CF_3)CF_2OCF(CF_3)COF$ (4992 g) was added and stirred, and maintained at 20° C. At the gas outlet of the autoclave, a cooler maintained at 0° C. was installed. After supplying nitrogen gas for 2.0 hours, fluorine gas diluted to 50% with nitrogen gas (hereinafter referred to as 50% fluorine gas) was supplied at a flow rate of 50.10 L/h for 2.0 hours.

Then, the internal temperature of the autoclave was brought to 25° C., and while supplying 50% fluorine gas at the same flow rate, the liquid mixture containing $(CH_3)_2CHOCOCF(CF_3)OCF_2CF(CF_3)OCF_2CF_2CF_3$ (208 g) obtained in Example 3-1 was injected over a period of 3.5 hours, and then the reaction crude liquid (262 g) was withdrawn (operation 1). Operations 2 to 8 as identified in the following Table were carried out in the same manner.

TABLE 2

| Operation | Amount injected (g) | Injection time (hr) | Reaction crude liquid | Yield (%) |
|---|---|---|---|---|
| 1 | 208 | 3.5 | 262 g | 41 |
| 2 | 202 | 4.0 | 264 | 55 |
| 3 | 235 | 4.0 | 527 | 67 |
| 4 | 466 | 8.0 | 534 | 82 |
| 5 | 282 | 4.0 | 532 | 85 |
| 6 | 450 | 8.0 | 266 | 88 |
| 7 | 219 | 4.0 | 265 | 87 |
| 8 | 456 | 8.0 | 271 | 90 |

In the reactor after completion of the operation 8, 4950 g of the reaction crude liquid remained. The reaction crude liquids withdrawn in the operations 1 to 8 were put together and analyzed by GC-MS, and as a result, a mixture containing $CF_3CF_2CF_2OCF(CF_3)CF_2OCF(CF_3)COF$ and the above-identified compound as the main components was confirmed. The yields by GC of the above-identified compound contained in the reaction crude liquids withdrawn in the respective operations are shown in Table.

Example 4

Example for Preparation of $CF_3CF_2CF_2OCF(CF_3)CF_2OCOCF(CF_3)OCF_2CF_2CF_3$

Into a 4L autoclave reactor made of nickel, $CF_3CF_2CF_2OCF(CF_3)COF$ (5113 g) was added and stirred, and maintained at 20° C. At the gas outlet of the autoclave, a cooler maintained at 0° C. was installed. After supplying nitrogen gas for 1.5 hours, 50% fluorine gas was supplied at a flow rate of 100.37 L/h for 1.5 hours.

Then, the internal temperature of the autoclave was brought to 25° C., and while supplying 50% fluorine gas at the same flow rate, the liquid mixture containing $CH_3CH_2CH_2OCH(CH_3)CH_2OCOCF(CF_3)OCF_2CF_2CF_3$ (190 g) obtained by the same redaction as in Example 1-1 was injected over a period of 8 hours, and then the reaction crude liquid (262 g) was withdrawn (operation 1). Operations 2 to 7 as identified in the following Table were carried out in the same manner.

TABLE 3

| Operation | Amount injected (g) | Injection time (hr) | Reaction crude liquid | Yield (%) |
|---|---|---|---|---|
| 1 | 190 | 8.0 | 262 | 78 |
| 2 | 435 | 4.0 | 261 | 90 |
| 3 | 335 | 8.0 | 264 | 91 |
| 4 | 808 | 18.0 | 264 | 93 |
| 5 | 275 | 8.0 | 265 | 93 |
| 6 | 357 | 8.0 | 264 | 95 |
| 7 | 372 | 8.0 | 295 | 95 |

In the reactor after completion of the operation 7, 4720 g of the reaction crude liquid remained. The reaction crude liquids withdrawn in the operations 1 to 7 were analyzed by GC-MS and as a result, a mixture containing $CF_3CF_2CF_2OCF(CF_3)COF$ and the above-identified compound as the main components was confirmed. The yields by GC of the above-identified compound contained in the reaction crude liquids withdrawn in the respective operations are shown in Table.

Example 5

Example 5-1

Example for Preparation of a Liquid Mixture of $CH_2=CHCH_2OCH_2CH_2CH_2OCOCF(CF_3)OCF_2CF(CF_3)OCF_2CF_2CF_3$ and $CF_3CF_2CF_2OCF(CF_3)CF_2OCF(CF_3)COF$ By using $CH_2=CHCH_2OCH_2CH_2CH_2OH$ (11.6 kg) and $CF_3CF_2CF_2OCF(CF_3)CF_2OCF(CF_3)COF$ (50.8 kg), the same reaction as in Example 1-1 was carried out to obtain the above-identified liquid mixture. The purity of $CH_2=CHCH_2OCH_2CH_2CH_2OCOCF(CF_3)OCF_2CF(CF_3)OCF_2CF_2CF_3$ was 98% as measured by GC.

Example 5-2

Example for Preparation of $CF_3CF_2CF_2OCF_2CF_2CF_2OCOCF(CF_3)OCF_2CF(CF_3)OCF_2CF_2CF_3$ Into a 4 L autoclave reactor made of nickel, $CF_3CF_2CF_2OCF(CF_3)CF_2OCF(CF_3)COF$ (5003 g) was added and stirred, and maintained at 25° C. At the gas outlet of the autoclave, a cooler maintained at −10° C. was installed. After supplying nitrogen gas for 2.0 hours, 50% fluorine gas was supplied at a flow rate of 65.33 L/h for 1.0 hour.

Then, while supplying 50% fluorine gas at the same flow rate, the liquid mixture containing $CH_2=CHCH_2OCH_2CH_2CH_2OCOCF(CF_3)OCF_2CF(CF_3)OCF_2CF_2CF_3$ (214 g) obtained by the method of Example 5-1 was injected over a period of 8 hours, and then the reaction crude liquid (264 g) was withdrawn (operation 1). Operations 2 to 10 as identified in the following Table were carried out in the same manner. Here, in the operation 3 and the subsequent operations, the flow rate of 50% fluorine gas was changed to 98.00 L/h.

TABLE 4

| Operation | Amount injected (g) | Injection time (hr) | Reaction crude liquid | Yield (%) |
|---|---|---|---|---|
| 1 | 214 | 8.0 | 264 | 80 |
| 2 | 331 | 12.0 | 261 | 75 |
| 3 | 258 | 8.0 | 263 | 84 |
| 4 | 136 | 4.0 | 262 | 77 |
| 5 | 147 | 4.0 | 260 | 75 |
| 6 | 374 | 8.0 | 263 | 77 |
| 7 | 168 | 4.0 | 265 | 77 |
| 8 | 166 | 4.0 | 266 | 78 |
| 9 | 140 | 4.0 | 270 | 79 |
| 10 | 705 | 16.0 | 268 | 78 |

In the reactor after completion of the operation 10, 4770 g of the reaction crude liquid remained. The reaction crude liquids withdrawn in the operations 1 to 10 were put together and analyzed by GC-MS, and as a result, a mixture containing $CF_3CF_2CF_2OCF(CF_3)CF_2OCF(CF_3)COF$ and the above-identified compound as the main components was confirmed. The yields by GC of the above-identified compound contained in the reaction crude liquids withdrawn in the respective operations are shown in Table.

Example 6

Example 6-1

Example for Preparation of $CH_2$=$CHCH_2CH(CH_3)OCOCF(CF_3)OCF_2CF_2CF_3$ $CH_2$=$CHCH_2CH(CH_3)OH$ (13.08 kg) was put in a reactor, and stirred while bubbling nitrogen gas. $FCOCF(CF_3)OCF_2CF_2CF_3$ (54.29 kg) was charged over a period of 5 hours while maintaining the internal temperature at from 25 to 30° C. After completion of the charging, while bubbling nitrogen gas, stirring was carried out at an internal temperature of from 30 to 50° C. for 70 hours.

The obtained crude liquid (58.32 kg) was used in the following step without purification. The purity was 96.6% as measured by GC. The NMR spectrum data are as follows.

$^1$H-NMR(300.4 MHz, solvent:CDCl$_3$, standard:TMS) δ (ppm): 1.32(d, J=6.0 Hz, 3H), 2.30–2.50(m,2H), 5.07–5.21 (m,3H), 5.61–5.76(m,1H).

$^{19}$F-NMR(282.7 MHz, solvent CDCl$_3$, standard:CFCl$_3$) δ (ppm): −79. 6(1F), −81.3(3F), −82.0(3F), −86.3(1F), −129.4 (2F), −131.5(1F).

Example 6-2

Example for Preparation of $CF_3CF_2CF_2OCF(CF_3)COOCH(CH_3)CH_2CHClCH_2Cl$

Into a 5 L flask equipped with a reflux condenser at 20° C., the crude liquid containing $CF_3CF_2CF_2OCF(CF_3)COOCH(CH_3)CH_2CH$=$CH_2$ (5000 g) obtained in Example 6-1 was charged, and the reactor was cooled to −30° C. Then, Cl$_2$ was continuously supplied and bubbled to the reaction liquid, and the supply rate of Cl$_2$ was controlled so that the temperature increase due to the heat of reaction would be at most 10° C. When the reaction proceeded and no heat generation was observed, the reaction was terminated. After completion of the reaction, the temperature of the reactor was brought to room temperature, and nitrogen gas was bubbled to the reaction liquid for 24 hours to remove excess Cl$_2$ by purging to obtain a crude liquid (5900 g) containing $FCOCF(CF_3)OCF_2CF_2CF_3$ and the above-identified compound. As a result of GC analysis, the yield of $CF_3CF_2CF_2OCF(CF_3)COOCH(CH_3)CH_2CHClCH_2Cl$ was 95%.

Example 6-3

Example for Preparation of $CF_2ClCFClCF_2CF(CF_3)OCOCF(CF_3)OCF_2CF_2CF_3$

Into a 4 L autoclave reactor-made of nickel, $CF_3CF_2CF_2OCF(CF_3)COF$ (4732 g) as a solvent was added and stirred, and maintained at 25° C. At the gas outlet of the autoclave, a cooler maintained at −10° C. was installed. After supplying nitrogen gas for 2.0 hours, 20% fluorine gas was supplied at a flow rate of 144.30 L/h for 1.0 hour.

Then, while supplying 20% fluorine gas at a flow rate of 144.30 L/h, the crude liquid containing $CF_3CF_2CF_2OCF(CF_3)COOCH(CH_3)CH_2CHClCH_2Cl$ (740 g) obtained by the method of Example 6-2 was injected over a period of 22 hours, and then the reaction crude liquid (820 g) was withdrawn (operation 1). The purity by GC of the above-identified compound contained in the reaction crude liquid (excluding the solvent) was 28%. Operations 2 to 7 as identified in the following Table were carried out in the same manner. In the reactor after completion of the operation 7, 3731 g of the reaction crude liquid remained.

TABLE 5

| Operation | Amount injected (g) | Injection time (hr) | Fluorine gas flow rate (L/h) | Reaction crude liquid (g) | Purity (%) |
|---|---|---|---|---|---|
| 1 | 740 | 22 | 144.30 | 840 | 28 |
| 2 | 765 | 21 | 80.57 | 1107 | 39 |
| 3 | 783 | 24 | ↑ | 1117 | 49 |
| 4 | 760 | 24 | 106.46 | 844 | 56 |
| 5 | 992 | 30 | ↑ | 1133 | 62 |
| 6 | 326 | 11 | 111.03 | 288 | 65 |
| 7 | 1161 | 42 | ↑ | 1145 | 71 |

Example 7

Example 7-1

Preparation of CHCl=CClO(CH$_2$)$_5$OH

Into a 500 mL four-necked flask, tetrahydrofuran (THF, 160 mL) and sodium hydride (60%, 24 g) were charged and stirred, and HO(CH$_2$)$_5$OH (260 g) was dropwise added thereto under cooling with ice. After completion of the dropwise addition, stirring was carried out at room temperature for 1 hour. Then, CHCl=CCl$_2$ (66 g) was dropwise added thereto over a period of 5 minutes. After completion of the dropwise addition, stirring was carried out at a bath temperature of 70° C. for 2.5 hours. After the mixture was left to cool, water (400 mL) and methylene chloride (400 mL) were added thereto under cooling with ice, followed by liquid separation to obtain a methylene chloride layer as an organic layer. Further, the organic layer was washed with water (400 mL) and dried to separate the above-identified compound. The results of analysis of the above-identified compound are as follows.

$^1$H-NMR(300.4 MHz, solvent:CDCl$_3$, standard:TMS) δ (ppm):1.37–1.79(m, 6H), 3.64(t,J=6.3 Hz, −2H), 4.00(t, J=6.5 Hz, 2H), 5.47(s, 1H)

Example 7-2

Example for Preparation of CHCl=CClO (CH$_2$)$_5$ OCOCF(CF$_3$)OCF$_2$CF(CF$_3$)CF$_2$OCF$_2$CF$_3$ CHCl=CClO(CH$_2$)$_5$OH (1.3 kg) obtained in the same method as in Example 7-1 and triethylamine (2.5 kg) were put in a reactor, and stirred under cooling with ice. CF$_3$CF$_2$CF$_2$OCF(CF$_3$)CF$_2$OCF(CF$_3$)COF (3.4 kg) was dropwise added thereto over a period of 10 hours while maintaining the internal temperature to be at most 10° C. After completion of the dropwise addition, stirring was carried out at room temperature for 2 hours, and 30 L of water was added thereto at an internal temperature of at most 15° C.

The obtained crude liquid was subjected to liquid separation, and the lower layer was washed with 50 L of water twice, followed by liquid separation, dehydration with a molecular sieve and filtration to obtain the above-identified liquid mixture. The purity by GC of the above-identified compound was 92%.

The results of analysis of CHCl=CClO(CH$_2$)$_5$OCOCF (CF$_3$)OCF$_2$CF(CF$_3$)CF$_2$OCF$_2$CF$_3$ are as follows.

$^1$H-NMR(300.4 MHz, solvent:CDCl$_3$, standard:TMS) δ (ppm):1.41–1.83(m, 6H), 4.00(t, J=6.0 Hz, 2H), 4.29–4.45 (m, 2H), 5.48(s, 1H)

$^{19}$F-NMR(282.7 MHz, solvent:CDCl$_3$, standard:CFCl$_3$) δ (ppm): −79. 9(1F), −81.4(3F), −82.2(3F), −86.5(1F), −129.5 (2F), −131.5(1F).

Example 7-3

Example for Preparation of CF$_2$ClCFClO(CF$_2$)$_5$ OCOCF(CF$_3$)OCF$_2$CF(CF$_3$)CF$_2$CF$_2$CF$_3$ Into a 3 L autoclave made of nickel, CF$_3$CF$_2$CF$_2$OCF (CF$_3$)CF$_2$OCF(CF$_3$)COF (3807 g) was added and stirred, and maintained at 20° C. At the gas outlet of the autoclave, a cooler maintained at −10° C. was installed. After supplying nitrogen gas for 1.5 hours, 20% fluorine gas was supplied at a flow rate of 205.23 L/h for 1.5 hours.

Then, the internal temperature of the autoclave was brought to 25° C., and while supplying 20% fluorine gas at the same flow rate, CHCl=CClO(CH$_2$)$_5$OCOCF(CF$_3$) OCF$_2$CF(CF$_3$)CF$_2$CF$_2$CF$_3$ (169 g) obtained in Example 7-2 was injected over a period of 5 hours, and then the reaction crude liquid (262 g) was withdrawn (operation 1). Operations 2 to 6 as identified in the following Table were carried out in the same manner.

TABLE 6

| Operation | Amount injected (g) | Injection time (hr) | Reaction crude liquid | Yield (%) |
|---|---|---|---|---|
| 1 | 169 | 5.0 | 262 | 41 |
| 2 | 137 | 4.0 | 265 | 43 |
| 3 | 432 | 12.0 | 267 | 45 |
| 4 | 180 | 4.0 | 269 | 54 |
| 5 | 182 | 4.0 | 268 | 54 |
| 6 | 185 | 4.0 | 267 | 62 |

In the reactor after completion of the operation 6, 3386 g of the reaction crude liquid remained. The reaction crude liquids withdrawn in the operations 1 to 6 were put together and analyzed by GC-MS, and as a result, a mixture containing CF$_3$CF$_2$CF$_2$OCF(CF$_3$)CF$_2$OCF(CF$_3$)COF and the above-identified compound as the main components was confirmed. The yields by GC of the above-identified compound contained in the reaction crude liquids withdrawn in the respective operations are shown in Table.

Example 8

Example for Preparation of CF$_2$ClCFClCF$_2$CF$_2$OCOCF$_2$CFClCF$_2$Cl

Into a 4 L autoclave reactor made of nickel, CF$_2$ClCFClCF$_2$COF (3600 g) as a solvent was added and stirred, and maintained at 25° C. At the gas outlet of the autoclave, a cooler maintained at −10° C. was installed. After supplying nitrogen gas for 2.0 hours, 50% fluorine gas was supplied at a flow rate of 201.42 L/h for 1.0 hour. Then, while supplying 20% fluorine gas at a flow rate of 201.42 L/h, the internal temperature of the reactor was changed to 5° C., a liquid mixture containing CH$_2$ClCHClCH$_2$CH$_2$OCOCF$_2$CFClCF$_2$Cl (590 g) and CF$_2$ClCFClCF$_2$COF was injected over a period of 18 hours, and the reaction crude liquid (534 g) was withdrawn (operation 1). The purity by GC of the above-identified compound contained in the reaction crude liquid (excluding the solvent) was 11%. Operations 2 to 6 as identified in the following Table were carried out in the same manner.

TABLE 7

| Operation | Amount injected (g) | Injection time (hr) | Fluorine gas flow rate (L/h) | Reaction crude liquid (g) | Purity (%) |
|---|---|---|---|---|---|
| 1 | 590 | 18 | 201.42 | 534 | 11 |
| 2 | 662 | 16 | 258.50 | 538 | 18 |
| 3 | 663 | 16 | ↑ | 810 | 31 |
| 4 | 718 | 22 | 201.42 | 818 | 48 |
| 5 | 638 | 20 | ↑ | 564 | 55 |
| 6 | 717 | 24 | ↑ | 564 | 61 |

Then, while maintaining the internal temperature of the reactor at 25° C., fluorine gas diluted to 20% with nitrogen gas was supplied at a flow rate of 240.57 L/h for 24 hours, and fluorine gas diluted to 50% with nitrogen gas was further supplied at a flow rate of 95.84 L/h for 8 hours. Then, 270 g of the reaction crude liquid was withdrawn. The purity of the above-identified compound contained in the reaction crude liquid was 70% (excluding the solvent).

Then, fluorine gas diluted to 50% with nitrogen gas was supplied at a flow rate of 126.26 L/h, and while maintaining the internal temperature of the reactor at 25° C., a liquid mixture containing CH$_2$ClCHClCH$_2$CH$_2$OCOCF$_2$CFClCF$_2$Cl (249 g) and CF$_2$ClCFClCF$_2$COF was injected over a period of 10 hours. 275 g of the reaction crude liquid was withdrawn. In the reactor, 2634 g of the reaction crude liquid remained. The purity of the above-identified compound contained in the reaction crude liquid was 86% (excluding the solvent).

INDUSTRIAL APPLICABILITY

According to the method of the present invention, a fluorinated ester compound can be produced with a high yield by carrying out a fluorination reaction of an ester compound in the presence of a compound having acyl fluoride group(s), which is excellent in solubility of the ester compound and which may act also as a liquid phase for the fluorination reaction.

A liquid mixture of the ester compound used for the fluorination reaction and the compound having acyl fluoride group(s) can be obtained by esterification of a compound having acyl fluoride group(s) in an excess amount and a compound having hydroxyl group(s). The esterification is favorable also from the viewpoint that the amount of the hydroxyl group-containing compound remaining in the reaction product can be decreased. Further, there is such an advantage that a purification step after the esterification can be simplified.

Further, the fluorination reaction product may be a mixture of a fluorinated ester compound and the compound having acyl fluoride group(s). In a case where the fluorinated ester compound is e.g. the compound (4) in which the ester bond may be dissociated, a method of carrying out the dissociation reaction by directly using the product of the fluorination reaction is an efficient method.

Further, in the method of the present invention, when groups are selected so that $R^{AF}$ and $R^{BF}$ are the same, the fluorinated ester compound (5A) formed by the dissociation reaction of the ester bond and the compound (2) are the same compound, whereby separation and purification of the product can be simplified.

Further, a method of using the compound (2) obtained from the product of the dissociation reaction of the ester bond of the compound (4) as the compound (2) to be reacted with the compound (1), is a favorable method as a method of continuously producing desired compounds (4) and (5) with a good efficiency.

Further, the method of the present invention is a method which can be carried out without preparing a solvent for each reaction. Further, it is a method which can be carried out without separating the solvent, when the following step is carried out, prior to the step. Further, it is a favorable method which can be carried out without using an environmentally unfavorable solvent such as R-113.

The entire disclosure of Japanese Patent Application No. 2000-295141 filed on Sep. 27, 2000 including specification, claims and summary is incorporated herein by reference in its entirety.

What is claimed is:

1. A method for producing a fluorinated ester compound, which comprises:
   esterifying a first compound having at least one hydroxyl group with a second compound having at least one acyl fluoride group to obtain a liquid mixture comprising an ester compound having a fluorine content of at least 30 mass % and a second compound,
   adding fluorine gas to the liquid mixture in an amount that is at least 1.5 mol equivalents when compared to the ester compound; and
   contacting the ester compound with fluorine gas to obtain the fluorinated ester compound.

2. The method according to claim 1, wherein the amount of the second compound is greater than the stoichiometric amount which is required to esterify all the hydroxyl groups in the first compound, and wherein a liquid phase comprises any unreacted second compound.

3. The method according to claim 1, wherein second compound is represented by formula (2), the ester compound is represented by formula (3), and the fluorinated ester compound is represented by formula (4):

$$FCOR^{BF} \quad (2)$$

$$R^{A}CHR^{1}OCOR^{BF} \quad (3)$$

$$R^{AF}CFR^{1F}OCOR^{BF} \quad (4)$$

wherein each of $R^{A}$ and $R^{AF}$ which may be the same or different, is a monovalent organic group, and when $R^{A}$ and $R^{AF}$ are different from each other, $R^{AF}$ is a monovalent organic group obtained by fluorination of $R^{A}$. $R^{BF}$ is a perfluoro monovalent saturated organic group. $R^{1}$ is a hydrogen atom or a monovalent organic group. $R^{1F}$ is a fluorine atom when $R^{1}$ is a hydrogen atom, when $R^{1}$ is a monovalent organic group, each of $R^{1}$ and $R^{1F}$ which may be the same or different, is a monovalent organic group, and when $R^{1}$ and $R^{1F}$ are different from each other, $R^{1F}$ is a monovalent organic group obtained by fluorination of $R^{1}$.

4. The method according to claim 3, wherein the first compound is represented by formula (1)

$$R^{A}CHR^{1}OH \quad (1);$$

wherein $R^{A}$ and $R^{1}$ are as defined above and
   wherein the amount of the second compound (2) is greater than the stoichiometric amount which is required to esterify all the hydroxyl groups in the first compound (1).

5. The method according to claim 3, which further comprises
   dissociating the ester bond of the ester compound represented by formula (4) to obtain a compound represented by the formula (5) and/or the second compound (2):

$$R^{AF}COR^{1F} \quad (5)$$

$$R^{BF}COF \quad (2)$$

wherein $R^{AF}$ and $R^{1F}$ are as defined above.

6. The method according to claim 5, wherein the dissociating occurs in a liquid phase comprising the second compound (2) and the fluorinated ester compound (4).

7. The method according to claim 6, wherein the dissociating occurs without adding a solvent to the liquid phase.

8. The method according to claim 4, wherein a part or whole of the compound (2) is obtained by a process which comprises:
   dissociating the ester bond of the fluorinated ester compound (4) to obtain a compound represented by formula (5) and/or the second compound (2):

$$R^{AF}COR^{1F} \quad (5)$$

$$R^{BF}COF \quad (2)$$

wherein $R^{AF}$ and $R^{1F}$ are as defined above;
   or whenever $R^{1F}$ is a fluorine atom, a part or whole of the compound (5) and/or the second compound (2).

9. The method according to claim 3, wherein $R^{AF}$ and $R^{BF}$ are groups having the same structure.

10. The method according to claim 3, wherein the contacting occurs in the absence of a solvent other than the second compound (2).

11. The method according to claim 1, wherein the ester compound has a fluorine content of from 30 to 86 mass %.

12. The method according to claim 1, wherein the ester compound has a fluorine content of from 30 to 76 mass %.

* * * * *